United States Patent
Takagaki et al.

(10) Patent No.: US 7,939,623 B2
(45) Date of Patent: May 10, 2011

(54) COMPOSITION CONTAINING FLAVAN COMPOUND

(75) Inventors: Kinya Takagaki, Fukuoka (JP); Takeshi Mitsui, Fukuoka (JP)

(73) Assignee: Toyo Shinyaku Co., Ltd., Fukuoka (JP)

( * ) Notice: Subject to any disclaimer, the term of this patent is extended or adjusted under 35 U.S.C. 154(b) by 531 days.

(21) Appl. No.: 11/667,892

(22) PCT Filed: Nov. 17, 2004

(86) PCT No.: PCT/JP2004/017438
§ 371 (c)(1),
(2), (4) Date: May 16, 2007

(87) PCT Pub. No.: WO2006/054363
PCT Pub. Date: May 26, 2006

(65) Prior Publication Data
US 2007/0293415 A1    Dec. 20, 2007

(51) Int. Cl.
*C07K 14/00* (2006.01)
*A61K 38/02* (2006.01)

(52) U.S. Cl. .......................... 530/300; 514/1.1; 514/21.2

(58) Field of Classification Search .................. None
See application file for complete search history.

(56) References Cited

U.S. PATENT DOCUMENTS

| | | | |
|---|---|---|---|
| 4,797,421 A | 1/1989 | Ariga et al. | |
| 6,045,849 A | 4/2000 | Ariga et al. | |
| 6,333,304 B1 | 12/2001 | Bath et al. | |
| 2003/0211183 A1* | 11/2003 | Takahashi et al. | 424/770 |

FOREIGN PATENT DOCUMENTS

| | | |
|---|---|---|
| JP | 61016982 A | 1/1986 |
| JP | 2134309 A | 5/1990 |
| JP | 2163046 A | 6/1990 |
| JP | 3168046 A | 7/1991 |
| JP | 6336423 A | 12/1994 |
| JP | 9009872 A | 1/1997 |
| JP | 11075708 A | 3/1999 |
| JP | 2000060482 A | 2/2000 |
| JP | 2001008634 A | 1/2001 |
| JP | 2002027957 A | 1/2002 |
| JP | 2002051734 A | 2/2002 |
| JP | 2002238497 A | 8/2002 |
| JP | 2004290102 A | 10/2004 |
| JP | 2004292378 A | 10/2004 |
| JP | 2004346132 A | 12/2004 |

OTHER PUBLICATIONS

Moskowitz RW, "Role of collagen hydrolysate in bone and joint disease," Seminars in Arthritis Rheumatism, Oct. 2000, 30(2): 87-99. Abstract only.*
Carter WA, Interferon: Evidence for Subunit Structure, Proceedings of the National Academy of Sciences, Oct. 1970, 67(2): 620-628.*
Alpha-lactalbumin molecular weight from http://www.sigmaaldrich.com/catalog/ProductDetail.do?N4=M6539|SIGMA&N5=SEARCH_CONCAT_PNO|BRAND_KEY&F=SPEC, pp. 1-2. Accessed Mar. 4, 2009.*
Translation of JP 2002027957, publication date, Jan. 29, 2002, pp. 1-25. Translated on Mar. 2009 by FLS, Inc.*
Translation of H07-009872, publication date Jan. 14, 1997. Translated on Mar. 2009 by USPTO Translation Branch.*

* cited by examiner

*Primary Examiner* — Julie Ha
(74) *Attorney, Agent, or Firm* — The Webb Law Firm

(57) ABSTRACT

A composition comprising: a flavan compound that is at least one of a proanthocyanidin and catechins; a protein degradation peptide having an average molecular weight of less than 7,000; and a peptide or protein having an average molecular weight of not less than 7,000. The composition does not impair effects of the flavan compound to the body. Furthermore, when the composition is formulated in a liquid preparation, neither coagulation-precipitation attributable to the nature of the flavan compound, nor coagulation-precipitation with the high molecular weight peptide or protein which is attributable to the protein-constricting property of the flavan compound is caused.

4 Claims, No Drawings

COMPOSITION CONTAINING FLAVAN COMPOUND

TECHNICAL FIELD

The present invention relates to a composition containing a flavan compound that is at least one of a proanthocyanidin and catechins, the composition in a liquid form, and a method for producing the liquid composition.

BACKGROUND ART

A flavan compound such as a proanthocyanidin and catechins is a polyoxy derivative (flavanonol) having a flavan skeleton, or polymer thereof, and classified as a condensed tannin group. From a long time ago, a flavan compound has been used industrially for leather tanning, and in cosmetics in order to provide a skin conditioning effect by improving astringency of the skin, for example. Recently, a flavan compound has been used in foods, cosmetics, and the like, because of its various activities such as an antioxidation properties and a whitening effect (Japanese Laid-Open Patent Publication No. S61-16982 and Japanese Laid-Open Patent Publication No. H2-134309). For example, a cosmetic article is known in which a protein (e.g., collagen) such as a collagen is blended with a flavan compound such as proanthocyanidin (Japanese Laid-Open Patent Publication No. H11-75708, Japanese Laid-Open Patent Publication No. 2000-60482, Japanese Laid-Open Patent Publication No. H6-336423, and Japanese Laid-Open Patent Publication No. 2002-238497).

However, a flavan compound has an extremely high ability to bind to a protein. Thus, when a flavan compound is extracted from a plant, it may be bound to a protein also included, so as to cause coagulation-precipitation, suspension, gelatinization, or the like, depending on factors such as the type of the plant and the method of extraction.

Recently, a flavan compound such as a proanthocyanidin has been used for producing gelatin gel having a high melting point or as a crosslinking agent of collagen, utilizing its high ability to bind to protein (Japanese Laid-Open Patent Publication No. H2-163046 and Japanese Laid-Open Patent Publication No. 2001-8634). However, usually, a flavan compound may causes a problem due to this ability in foods, drugs, quasi-drugs, cosmetics, and the like.

For example, once a flavan compound is coagulated and precipitated, or gelled with protein in a solution during the manufacturing process, a proanthocyanidin or protein must be degraded by treatments such as an acid treatment or an alkali treatment in order to dissolve them again. Thus, it is difficult to produce articles such as foods, drugs, quasi-drugs, and cosmetics containing these components. Furthermore, even if these articles can be produced, there is a problem that coagulation-precipitation may be caused during a storage period in a case of formulated in a liquid preparation such as beverage or skin lotion.

In order to address these problems, Japanese Laid-Open Patent Publication No. 2002-51734 has disclosed an improved method for enhancing the stabilities of tannin, which is a flavan compound, and collagen, which is protein, in a solution. However, this method has a problem that collagen used is limited to low molecular weight collagen peptides.

DISCLOSURE OF INVENTION

It is an object of the present invention to provide a flavan compound-containing composition and a method for producing the composition in a liquid form, for addressing a problem attributable to the protein-constricting property of the flavan compound, that is, a problem that a flavan compound may cause coagulation-precipitation or gelation with a peptide or protein having a relatively high molecular weight.

Surprisingly, the inventors of the present invention found that any coagulation-precipitation can not be caused when a composition containing a flavan compound that is at least one of a proanthocyanidin and catechins, a protein degradation peptide having a low molecular weight within a specific range, and a peptide or protein having a relatively high molecular weight within a specific range is dissolved in a solvent such as water, and that as a result, a liquid preparation having long term stability can be easily produced, and thus the present invention was achieved.

The flavan compound-containing composition of the present invention includes a flavan compound that is at least one of a proanthocyanidin and catechins; a protein degradation peptide having an average molecular weight of less than 7,000; and a peptide or protein having an average molecular weight of not less than 7,000.

In a preferred embodiment, the proanthocyanidin comprises at least 1 part by weight of proanthocyanidins having a degree of polymerization of 2 to 4 with respect to 1 part by weight of proanthocyanidins having a degree of polymerization of 5 or more.

The flavan compound-containing liquid composition of the present invention includes a flavan compound that is at least one of a proanthocyanidin and catechins; a protein degradation peptide having an average molecular weight of less than 7,000; a peptide or protein having an average molecular weight of not less than 7,000; and a solvent.

In a preferred embodiment, the proanthocyanidin includes at least 1 part by weight of proanthocyanidins having a degree of polymerization of 2 to 4 with respect to 1 part by weight of proanthocyanidins having a degree of polymerization of 5 or more.

The present invention is directed to a method for producing the liquid composition, wherein the method includes the steps of mixing, in a solvent, a flavan compound that is at least one of a proanthocyanidin and catechins with a protein degradation peptide having an average molecular weight of less than 7,000; and adding a peptide or protein having an average molecular weight of not less than 7,000 to the obtained mixture and mixing them.

The present invention is directed to another method for producing the liquid composition, wherein the method includes the step of: dissolving coagulation-precipitation caused in a solution containing a flavan compound that is at least one of a proanthocyanidin and catechins and a peptide or protein having an average molecular weight of not less than 7,000 by adding and mixing a protein degradation peptide having an average molecular weight of less than 7,000 in the solution.

According to the present invention, a composition can be provided, wherein the composition includes a flavan compound, a protein degradation peptide having an average molecular weight of less than 7000, and a peptide or protein having an average molecular weight of not less than 7,000. In a case where the composition is formulated in a liquid preparation, the liquid preparation can be stable for a long period of time without coagulation-precipitation. Even if the precipitation is formed by either a flavan compound, or a flavan compound and a peptide or protein having a high molecular weight, the precipitation can be dissolved again by adding a protein degradation peptide having an average molecular weight of less than 7,000 to obtain a clear and stable solution.

Accordingly, it is possible to avoid a loss of any components caused by precipitation in production.

BEST MODE FOR CARRYING OUT THE INVENTION

Hereinafter, a composition and a method for producing the composition in a liquid form, according to the present invention, are described. It should be noted that the following description should not be construed as limiting the present invention, and it will be apparent to those skilled in the art that various modifications may be made to the present invention within the scope of the spirit of the present invention.

The flavan compound-containing composition of the present invention contains a flavan compound, protein degradation peptide having an average molecular weight of less than 7,000, and peptide having an average molecular weight of not less than 7,000. In a case where the composition is a liquid form, the composition contains a solvent. The composition can optionally contain other components in addition to the above. These components are described below.

(1) Flavan Compound

The flavan compound used in the present invention is at least one of a proanthocyanidin and catechins.

The proanthocyanidin refers to any compounds that are condensation products having flavan-3-ol and/or flavan-3,4-diol as a constituent unit and having a degree of polymerization of 2 or more. Proanthocyanidins are one kind of polyphenols, and a potent antioxidant produced by plants, and are contained abundantly in leaves, bark, skin of fruits or seeds of the plants. Proanthocyanidins cannot be produced in the human body.

Preferably, the proanthocyanidin including a large amount of condensation products having a low degree of polymerization is used. The condensation product having a low degree of polymerization is preferably condensation product having a degree of polymerization of 2 to 30 (dimer to 30-mer), more preferably condensation product having a degree of polymerization of 2 to 10 (dimer to decamer), and even more preferably condensation product having a degree of polymerization of 2 to 4 (dimer to tetramer). In this specification, the condensation product having a degree of polymerization of 2 to 4 is referred to as OPC (oligomeric proanthocyanidin). It is preferable that the proanthocyanidin comprises 1 part by weight or more of OPCs with respect to 1 part by weight of proanthocyanidins having a degree of polymerization of 5 or more. Although proanthocyanidins having a degree of polymerization of 5 or more tend to cause coagulation-precipitation when mixed with a peptide or protein having a higher molecular weight, coagulation-precipitation or suspension is hardly caused using the proanthocyanidin including OPCs at the above-defined ratio.

Specifically, any proanthocyanidins, in particular, OPCs are contained in: the bark of pine, oak, bayberry, and the like; the fruit or seeds of grape, blueberry, raspberry, cranberry, strawberry, avocado, locust, and cowberry; the hull of barley, wheat, soybean, black soybean, cacao, adzuki bean, and conker; the inner skin of peanuts; and the leaves of ginkgo, for example. Moreover, it is known that OPCs are contained in cola nuts in West Africa, the roots of Rathania in Peru, and Japanese green tea. Thus, proanthocyanidin-containing materials used as food materials, such as an extract from barks, fruits, or seeds as mentioned above, can be also used. In particular, it is preferable to use a pine bark extract. Pine bark is especially abundant in OPCs, and thus is preferably used as a proanthocyanidin-containing material.

When the extract from proanthocyanidin containing plant is used, it is preferable to use an extract from plant having a high OPC content. In the extract containing any proanthocyanidins, OPCs can be contained at a dry weight ratio of 20 wt % or more, preferably 30 wt % or more, and more preferably 50 wt % or more. Using such extracts, coagulation-precipitation or suspension is hardly caused as in the above-described case.

Since proanthocyanidins, in particular, OPCs are antioxidants as described above, they are known to have an effect of reducing the risk of adult diseases such as cancer, cardiac diseases, and cerebral thorombosis, and an effect of improving allergic diathesis such as arthritis, atopic dermatitis, and pollenosis. In addition to the antioxidation effect, OPCs are also known to have an effect of inhibiting bacterial proliferation in the oral cavity to reduce plaque (dental plaque), an effect of recovering the elasticity of blood vessels, an effect of improving skin type, an effect of enhancing collagen, an effect of improving hyperlipemia, an effect of preventing lipoprotein in blood from being damaged by active oxygen, thereby preventing aggregation and adherence of the oxidized fats onto the inside wall of the vessel, thus preventing cholesterol from being aggregated and adhered onto the oxidized fats that have been adhered onto the inside wall of the vessel, an effect of regenerating vitamin E that has been degraded by active oxygen, an effect of serving as an enhancer of vitamin E, and the like. Thus, the composition of the present invention can be used in the articles such as pharmaceutical and food products, for realizing these effects.

The term "catechins" is a general term of polyhydroxyflavan-3-ols. Examples of the catechins include (+)-catechin (which is referred to as "catechin" in a narrow sense), (−)-epicatechin, (+)-gallocatechin, (−)-epigallocatechin, epigallocatechin gallate, epicatechin gallate, and afzelechin. Furthermore, plant extracts containing catechins can used. Since catechins are often contained in plants together with proanthocyanidins, the plant extracts containing proanthocyanidins as mentioned above can be also used as catechins containing materials. In addition to (+)-catechin, gallocatechin, afzelechin, 3-galloyl derivatives of (+)-catechin, and 3-galloyl derivatives of gallocatechin are isolated from extracts derived from raw material plants such as pine bark.

Catechins are known to have a cancer inhibiting ability, an arteriosclerosis preventing ability, a lipid metabolism disorder inhibiting ability, a blood pressure elevation inhibiting ability, a platelet aggregation inhibiting ability, an antiallergic ability, an antiviral ability, an antibacterial ability, a dental caries preventing ability, a halitosis preventing ability, an intestinal flora normalization ability, an active oxygen or free radical eliminating ability, an antioxidation ability, and the like. Moreover, catechins are known to have an antidiabetic ability due to inhibiting an elevation of blood glucose. In the presence of OPCs, catechins have an increased water solubility and activate OPCs. Therefore, catechins enhance the abilities of OPCs when ingested together with the OPCs.

The flavan compound used in the present invention may be either one of a proanthocyanidin or catechins. It is preferable to use both of a proanthocyanidin (OPC) and catechins in the present invention in order to improve the solubility and bioactivity of OPC. It is more preferable that the composition contains 0.1 parts by weight or more of catechins with respect to 1 part by weight of proanthocyanidins. For example, it is preferable to use the plant extracts, which contains an OPC and catechins. The contents of proanthocyanidins and catechins may vary depending on the kind of plants, however, a pine bark extract, a grape extract, and the like have a high content of proanthocyanidins, and a tea leaf extract (e.g., green tea and black tea) has a high content of catechins. It is preferable to use a pine bark extract. The plant extracts preferably contain 20 wt % or more of OPCs and 5 wt % or more of catechins, in dry weight.

Hereinafter, a method for preparing the flavan compound is described taking, as an example, a pine bark extract that is abundant in OPCs and contains catechins.

As a pine bark extract, an extract from the bark of plants of Pinales, such as French maritime pine (*Pinus martima*), *Larix leptolepis, Pinus thunbergii, Pinus densiflora, Pinus parviflora, Pinus pentaphylla, Pinus koraiensis, Pinus pumila, Pinus luchuensis, utsukushimatsu* (*Pinus densiflora* form. *umbraculifera*), *Pinus palustris, Pinus bungeana*, and Anneda in Quebec, Canada, can be preferably used. Among these, French maritime pine (*Pinus martima*) bark extract is preferable. French maritime pine refers to maritime pines that grow in a part of the Atlantic coastal area in southern France. The bark of French maritime pine contains organic acids and other bioactive substances in addition to proanthocyanidins.

The pine bark extract is obtained by extracting from the bark of the pines as mentioned above using water or an organic solvent. When water is used, warm water or hot water is employed. As the organic solvent employed for extraction, organic solvents acceptable for production of foods or pharmaceuticals can be employed, and examples thereof include methanol, ethanol, 1-propanol, 2-propanol, 1-butanol, 2-butanol, acetone, hexane, cyclohexane, propylene glycol, aqueous ethanol, aqueous propylene glycol, methyl ethyl ketone, glycerin, methyl acetate, ethyl acetate, diethyl ether, dichloromethane, edible oils or fats, 1,1,1,2-tetrafluoroethane, and 1,1,2-trichloroethene. As the solvent for extraction, the water and organic solvents as mentioned above may be used alone or in combination. In particular, hot water, aqueous ethanol, and aqueous propylene glycol are preferably used.

The method for extracting is not particularly limited, and heat extraction or supercritical fluid extraction can be employed, for example.

Supercritical fluid extraction is a method for performing extraction using a supercritical fluid which is in a state that is above the liquid-vapor critical point in the phase diagram showing critical temperature and critical pressure. A supercritical fluid such as carbon dioxide, ethylene, propane, and nitrous oxide (laughter gas) can be used. Carbon dioxide is preferably used.

Supercritical fluid extraction includes an extraction step in which a target is extracted with a supercritical fluid and a separation step in which the target component is separated from the supercritical fluid. In the separation step, any separation process can be employed, examples of which include a separation based on a change in pressure, a separation based on a change in temperature, and a separation using an adsorbent or absorbent.

Moreover, the supercritical fluid extraction can be performed with the additional of entrainer. Specifically the supercritical fluid, extraction can be performed using fluid for extraction prepared by adding an entrainer, such as ethanol, propanol, n-hexane, acetone, toluene, or other aliphatic lower alcohols, aliphatic hydrocarbons, aromatic hydrocarbons, or ketones, at about 2 to 20 W/V % to a supercritical fluid, for dramatically increasing the solubility in a solvent for extraction of a target to be extracted, such as proanthocyanidins (OPCs) and catechins, or enhancing the selectivity of separation. Using this method, a pine bark extract can be obtained efficiently.

Since supercritical fluid extraction can be performed at a relatively low temperature, it has the following advantages: it is applicable for extracting substances that deteriorate or decompose at high temperatures; the fluid for extraction does not remain; and the fluid for extraction can be recovered and recycled so that the steps including a step of removing the extracting fluid can be omitted, and thus, the process can be simplified.

The extraction from pine bark can be performed using a batch method using liquid carbon dioxide, a reflux method using liquid carbon dioxide, a reflux method using supercritical carbon dioxide, or the like, other than those mentioned above.

The extraction from pine bark can be also performed employing the combination of a plurality of extraction processes. By combining a plurality of extraction processes, the pine bark extract can be obtained with various compositions.

The pine bark extract used in the composition of the present invention is specifically prepared using the following method. However, this method is merely an example, and there is not limited to this method.

First, 1 kg of the bark of French maritime pine is immersed in 3 L of a saturated solution of sodium chloride, and extraction is performed for 30 minutes at 100° C. to obtain an extract liquid (extraction step). Then, the extract liquid is filtrated, and the resultant insoluble material is washed with 500 ml of a saturated solution of sodium chloride to obtain a washed liquid (washing step). The extract liquid and the washed liquid are combined to obtain a crude extract liquid of pine bark.

Next, 250 ml of ethyl acetate is added to this crude extract liquid, mixed, and separated to obtain an ethyl acetate layer. This process is repeated additional four times, and the obtained ethyl acetate layers are combined. The resultant ethyl acetate extract is added directly to 200 g of anhydrous sodium sulfate for drying, and then filtrated. The filtrated extract is concentrated under a reduced pressure to a volume of ⅕ of the original filtrated extract. The concentrated ethyl acetate extract is poured into 2 L of chloroform and stirred, and the resultant precipitate is recovered by filtration. Subsequently, this precipitate is dissolved in 100 ml of ethyl acetate, and then the resultant solution is added to 1 L of chloroform to form a precipitate. This process is repeated again, and thus, a washing process is accomplished. According to the procedure as mentioned above, for example, about 5 g of pine bark extract containing at least 20 wt % of OPCs that is the condensation product having a degree of polymerization of 2 to 4 and at least 5 wt % of catechins can be obtained.

The extracts derived from raw material plants such as pine bark contain OPCs, at a dry weight ratio of preferably 20 wt % or more, and more preferably 30 wt % or more. As described above, the dry weight content of catechins is usually 5 wt % or more. However, when the content of catechins is less than 5-wt %, catechins may be added such that the content is 5 wt % or more. It is most preferable to use a pine bark extract that contains 5 wt % or more of catechins and 20 wt % or more of OPCs.

It should be noted that in a case where an extract is obtained from plants using a polar solvent such as water or ethanol as described above, the polar solvent can preferably dissolve proanthocyanidins having a relatively low molecular weight, to provide proanthocyanidins mainly including proanthocyanidins having a degree of polymerization of 20 or less, usually having a degree of polymerization of 10 or less.

The flavan compound is contained at a dry weight ratio of preferably 0.00001 wt % to 50 wt %, more preferably 0.001 wt % to 40 wt %, and even more preferably 0.01 wt % to 20 wt % in the composition.

(2) Protein Degradation Peptide Having an Average Molecular Weight of Less than 7000

The protein degradation peptide having an average molecular weight of less than 7,000, which is contained in the composition of the present invention, refers to any peptides obtainable by protein degradation which have an average molecular weight of less than 7,000 (herein, also may be referred to as "protein degradation peptide"). "Average molecular weight" herein refers to weight average molecular weight. The protein degradation peptide can be any peptides obtained by degrading various proteins derived from animals or plants using acid, alkali, or enzyme, but also may be any peptides obtained by organic synthesis. In the case of a protein degradation peptide derived from animals or plants, examples of starting proteins include: animal proteins, such as collagen (gelatin), which are derived from domestic animals such as cattle, swine, and chicken, fishes, animal milk, and eggs; and plant proteins derived from soybean, wheat, corn, and peas. As the starting proteins, it is particularly preferable to use collagen. As the protein degradation peptide, any collagen peptides are most preferable which are any products of collagen degradation.

Collagen is a primary protein which forms connective tissues of animals, and is contained abundantly in bone, tendon, skin, blood vessel wall, and the like. Collagen is composed of polypeptide chains and has one or two or more triple helical structure. There are various types of collagens depending on the amino acid sequence of the polypeptide chain. Gelatin is a modified product of collagen, and is a water-soluble protein obtainable by extracting from a collagen containing material with warm (hot) water which has a molecular weight of approximately 300 thousands to several tens of thousands. Examples of gelatin includes alkali-treated gelatin (isoelectric point: 4.8 to 5.3) and acid-treated gelatin (isoelectric point: 7 to 9).

A method for preparing a collagen peptide from collagen or gelatin is specifically described below. First, a pre-treatment is performed by soaking skins or bones of bovine, swine, or the like in an alkali solution for two to three months (i.e., alkali treatment), or in dilute hydrochloric acid or the like for a short period (i.e., acid treatment), for removing impurities in a raw material and facilitating extraction. For example, when bovine bones are used as the raw material, since the bones include inorganic matters such as calcium phosphate, the bones are soaked in a dilute hydrochloric acid in advance to remove the inorganic matters, and then warm (hot) water extraction is performed on the resultant, and thus gelatin is obtained. Usually, in the warm (hot) water extraction, a first extraction temperature is set to 50 to 60° C., the extraction temperature is gradually increased from the second and following extractions, and water is finally boiled. Subsequently, the obtained gelatin is hydrolyzed with acid or enzyme as commonly used to obtain a collagen peptide.

The thus obtained collagen peptide has an average molecular weight of less than approximately 7,000, and preferably approximately 6,000 or less. As the collagen peptide having the molecular weight as mentioned above, a peptide having a molecular weight of approximately 200 or more, preferably approximately 1,000 or more, more preferably 3,000 or more, and even more preferably approximately 5,000 or more can be used in order to achieve an effect of being stably dissolved together with a flavan compound in a solution, and an effect of preventing the precipitation of protein. If the average molecular weight is not less than 7,000, high molecular weight (decamer to 30-mer) proanthocyanidins may be bound to form precipitation or suspension.

The collagen peptide having the molecular weight as mentioned above is also commercially available. Examples of the products of collagen peptide derived from animal collagen include: Nippi Peptide PBF and Nippi Peptide PRA (both are produced by Nippi, incorporated), SCP-5000 and SCP-3100 (both are produced by Nitta Gelatin Inc.), Collagen peptide DS (produced by Kyowa Hi Foods Co., Ltd.), and Pharconix CTP (produced by Ichimaru Pharcos Co., Ltd.). As well as collagen peptides derived from animals, any peptides having an amino acid composition similar to that of animal collagen are preferable, and examples thereof include a peptide derived from carrot (*Daucus carota* L.).

The protein degradation peptide (preferably collagen peptide) is contained at a dry weight ratio of preferably 0.00001 wt % to 90 wt %, and more preferably 0.0001 wt % to 50 wt % in the composition.

(3) Peptide or Protein Having an Average Molecular Weight of not Less than 7,000

The peptide or protein having an average molecular weight of not less than 7,000 (hereinafter, may be referred to as "high molecular weight peptide or protein"), which is contained in the composition of the present invention, can be obtained from any sources, as long as the peptide or protein has an average molecular weight of not less than 7,000. Examples thereof include various animal proteins (e.g., collagen) and plant proteins, which are starting materials of the protein degradation peptide, modified products (e.g., gelatin, which is a modified product of collagen), and degraded peptides therefrom.

(4) Solvent

A solvent is used when preparing the flavan compound-containing liquid composition (described later) of the present invention. The solvent is usually water, and, if necessary, may further include a solvent, such as alcohol (e.g., ethanol or isopropanol), that can be mixed with water.

(5) Other Components

The composition of the present invention may contain, if necessary, other components within the range not impairing the effects of the composition, in addition to a flavan compound, a protein degradation peptide having a defined molecular weight, and a high molecular weight peptide or protein as defined above. Such components are commonly used in the articles such as foods, drugs, quasi-drugs, and cosmetics, and examples of the components include antioxidants, medicinal components, oils, humectants, surfactants, ultraviolet absorbers, absorption promoters, flavors, coloring agents, preservatives, thickeners, chelating agents, and antiseptic and antifungal agents.

Among the components, antioxidants are used in order to enhance the stability of the flavan compound. Thus, it is possible to achieve an effect of improving and protecting the skin, by preventing the oxidization of protein or lipid in the body.

Examples of antioxidants include carotinoids such as vitamin A, vitamins of B family, ascorbic acid, vitamin E, and derivatives or salts thereof, L-cysteine and derivatives or salts thereof, riboflavine, SOD, mannitol, tryptophan, histidine, quercetine, garlic acid and its derivatives, and extracts (e.g., tea extract, and glutathione yeast extract).

Among these, ascorbic acid not only enhances the stability of the flavan compound, but also synergically acts on the skin, thereby enhancing an effect improving the skin (e.g., an effect of improving suppleness and gloss of the skin), and an effect blood vessels protecting. There is no specific limitation regarding the content of ascorbic acid, but ascorbic acid may be contained in the composition of the present invention such that the weight ratio between the flavan compound and ascorbic acid is preferably 1:0.1 to 1:50, and more preferably 1:0.2 to 1:20.

Examples of the medicinal components include active oxygen removers, antiphlogistic sedative drugs, antihistamine drugs, antipruritic drugs, disinfectants, vitamin compounds, hormone drugs, and humectants.

(6) Composition Containing a Flavan Compound

As described above, the flavan compound-containing composition of the present invention contains (1) a flavan compound that is at least one of a proanthocyanidin and catechins, (2) a protein degradation peptide having an average molecular weight of less than 7,000, and (3) a peptide or protein having an average molecular weight of not less than 7,000. When the composition is a liquid composition (liquid preparation), the composition further contains (4) a solvent. In addition to the above, the composition may contain (5) other components, if necessary.

In the composition of the present invention, with respect to 1 part by weight of the flavan compound of (1) above on the basis of dry weight, the protein degradation peptide of (2) above is contained at a ratio of preferably 3 parts by weight or more, more preferably 5 parts by weight or more, and even more preferably 8 parts by weight or more. Furthermore, with respect to 1 part by weight of the protein degradation peptide of (2) above on the basis of dry weight, the high molecular weight peptide or protein of (3) above is contained at a ratio of preferably 3 parts by weight or less, more preferably 2 parts by weight or less, and even more preferably 1 part by weight or less. In a case where the composition is formulated in a liquid preparation, a larger content of the protein degradation peptide has a greater effect of inhibiting the coagulation caused by binding between the flavan compound and the high molecular weight peptide or protein, or of cleaving the binding that has been once generated. As a result, coagulation-precipitation (including gelatinization) can be prevented in the solvent. Moreover, in a case where the composition is formulated in a liquid composition (described later) as a product, the product can be stable for a long period of time without coagulation-precipitation. Furthermore, a smaller content of the high molecular weight peptide or protein less causes coagulation-precipitation.

In the composition as thus provided, when the protein degradation peptide and the high molecular weight peptide or protein are collectively taken as the total protein (peptide) contained in the composition, and the average molecular weight of the total protein is not less than 4,000, not less than 6000, or even not less than 7,000, coagulation-precipitation, suspension, or gelatinization is not formed or, if formed, can be dissolved again in a solution. Thus, the composition can be stored as a uniform solution.

The composition of the present invention may be in the form of a tablet or a powder, as well as the form of a liquid preparation.

The liquid preparation is obtained by mixing, in any order, components of above (1) to (4), and, optionally, above (5). Basically, it is preferable to mix a flavan compound and a protein degradation peptide in a solvent, and then to add a peptide or protein having an average molecular weight of not less than 7,000 to the resultant mixture and mix them. Accordingly, coagulation-precipitation is not caused in the mixing process, and a uniform solution can be obtained in a short time, so that it is possible to make the production efficient.

In a case where a flavan compound is first mixed with a peptide or protein having an average molecular weight of not less than 7,000 in a solvent, coagulation-precipitation would be easily caused in the resultant solution. In this case, the coagulation-precipitation can be dissolved by adding and mixing a protein degradation peptide in the solution with the coagulation-precipitation to provide a clear liquid preparation uniformly containing the components. It is useful for dissolving again coagulation-precipitation, suspension, or gelatinization formed by a flavan compound and a high molecular weight peptide or protein in a solvent in the production process.

In another embodiment, a protein degradation peptide is first mixed with a peptide or protein having an average molecular weight of not less than 7,000 in a solvent, and then a flavan compound is added and mixed with the mixture. In the case, coagulation-precipitation or locally gelatinization may be formed in the resultant solution, so that the components can not be uniformly mixed. The coagulation-precipitation or gelatinization can be disappeared by agitating the mixture for at least ten minutes or more, or preferably 30 minutes or more, or being allowed to stand for one day or more, and thus a uniform liquid preparation can be obtained without coagulation-precipitation.

The above-described composition can be produced in the form of a tablet, a powder, and the like by methods commonly used by those skilled in the art. The composition can be used in any of these forms, in the articles such as foods, drugs, quasi-drugs, and cosmetics.

(Effects)

As described above, the composition of the present invention contains a flavan compound, a protein degradation peptide having an average molecular weight of less than 7000, and a peptide or protein having an average molecular weight of not less than 7,000 (of a high molecular weight). It is possible to prevent coagulation-precipitation of a flavan compound and a high molecular weight peptide or protein in a solvent by inclusion of a protein degradation peptide in the composition. It is possible that the coagulation of a flavan compound by a high molecular weight peptide or protein can be cleaved or inhibited with a protein degradation peptide. Therefore, according to the composition of the present invention, coagulation-precipitation of a flavan compound and a high molecular weight peptide or protein is not formed or, if formed, can be dissolved again in the solvent. Thus, any treatments for re-dissolution such as acidlysis or alkalinolysis as conventionally performed are not necessary. Furthermore, since there is no loss of the components in production, a uniform solution can be obtained, so that it is possible to make the production of a liquid preparation efficient. According to the composition of the present invention, coagulation-precipitation is not caused, and thus, for example, in the case where a flavan compound and collagen are contained, an effect of enhancing the collagen, an effect of preventing the inhibition of bioactivity caused by coagulation of a flavan compound, and the like can be effectively exerted. The preservation stability of the product from a liquid preparation as mentioned above is good in that coagulation-precipitation is not caused. The composition of the present invention can be used in a wide range of applications such as foods, drugs, quasi-drugs, and cosmetics.

EXAMPLES

Hereinafter, the present invention will be described by way of examples, but it would be appreciated that the present invention is not limited to the following examples. In the examples, "average molecular weight" refers to weight average molecular weight.

Reference Example

Evaluation for Coagulation-precipitation of Flavan Compounds and Proteins (Peptides))

The coagulation-precipitation was evaluated on the mixtures using various flavan compounds and proteins. First, a column (50×500 mm) was filled with Sephadex LH-20 swollen with water at a column volume of 500 mL, and was washed with 500 mL of ethanol. Then, 10 g of a pine bark extract (proanthocyanidins having a degree of polymerization of 2 to 4 (OPCs): 40 wt %, proanthocyanidins having a degree of polymerization of 5 or more: 8.7 wt %, and catechins: 5.1 wt %, trade mark: Flavangenol, produced by Toyo Shinyaku Co., Ltd.) was dissolved in 200 mL of ethanol. This solution was applied on the column for adsorption of proanthocyanidins. Thereafter, gradient elution was conducted using 100 to 80% (v/v) ethanol-water mixed solvent, and the resultant eluate was collected in fractions of 100 mL each. Each fraction was examined for the presence of catechins and OPCs by silica gel chromatography (TLC) using standards of catechin (Rf value: 0.8) and dimer to tetramer OPC (dimer OPC: proanthocyanidin B-2 (Rf value: 0.6), trimer OPC: proanthocyanidin C-1 (Rf value: 0.4), tetramer OPC: cinnamtannin $A_2$ (Rf value: 0.2)) as indicators. The conditions of the TLC were as follows.

TLC: silica gel plate (produced by Merck & Co., Inc.)
Eluent: benzene/ethyl formate/formic acid (2/7/1)
Detection reagent: a mixture of sulfuric acid and anisaldehyde
Sample amount: 10 μL each Catechins were not detected in any fraction. Thus, it was confirmed that catechins were not contained in the fractions. Among the obtained fractions, a fraction in which OPCs were detected was taken as an OPC-containing fraction, and a fraction in which OPCs were not detected was taken as a fraction containing proanthocyanidins having a degree of polymerization of 5 or more, and these fractions were freeze-dried. By repeating this operation twice, 7.6 g of dry powder of OPCs and 1.6 g of dry powder of proanthocyanidins having a degree of polymerization of 5 or more were obtained. These dry powders were mixed, and a catechin-free, proanthocyanidin dry powder was obtained.

Then, an aqueous solution of each of the pine bark extract, the proanthocyanidin dry powder, and epigallocatechin (produced by Roche Vitamins Japan K.K.) was prepared such that a final concentration was 0.2 wt %, as a first liquid.

Separately, collagen (having an average molecular weight of 300 thousands: produced by KOKEN CO., LTD), Nippi Peptide PA-100 (having an average molecular weight of 10,000: produced by Nippi, incorporated), Collagen peptide DS (having an average molecular weight of 7,000: produced by Kyowa. Hi Foods Co., Ltd.), SCP-5000 (having an average molecular weight of 5,000: produced by Nitta Gelatin Inc.), Pharconics CTP (having an average molecular weight of 3,000: produced by Ichimaru Pharcos Co., Ltd.), Nippi Peptide PA-10 (having an average molecular weight of 1,000: produced by Nippi, incorporated), and glycine (having a molecular weight of 75: produced by Wako Pure Chemical Industries, Ltd.) were respectively dissolved in water to prepare an aqueous solution of each of them such that the content of collagen, collagen peptide, or amino acid was 10.0 wt %, as a second liquid.

At room temperature, 1 mL of first liquid and 1 mL of second liquid were mixed. The resultant liquid mixture was allowed to stand at room temperature for one week, and it was visually observed whether or not precipitation or suspension was caused in the liquid mixture. The results are shown in Table 1.

TABLE 1

| | | | Second liquid*[1] | | | | | | |
|---|---|---|---|---|---|---|---|---|---|
| | | | Glycine | Collagen peptide | | | | | Collagen |
| | | | 75 | 1,000 | 3,000 | 5,000 | 7,000 | 10,000 | 300,000 |
| First liquid | Pine bark extract | Precipitation | − | − | − | − | − | + | + |
| | | Suspension | − | − | − | − | ± | + | + |
| | Proanthocyanidins | Precipitation | − | − | − | − | − | + | + |
| | | Suspension | − | − | − | − | ± | + | + |
| | Epigallocatechin gallate | Precipitation | − | − | − | − | − | ± | + |
| | | Suspension | − | − | − | − | − | + | + |

+: The precipitation was remarkably observed, ±: The precipitation was slightly observed, −: Not observed.
*[1]Values in average molecular weight As shown in Table 1, suspension and precipitation were caused in all of the flavan compounds when mixed with an aqueous solution containing collagen peptide having an average molecular weight of 10,000 or collagen having an average molecular weight of 300,000. In particular, in mixtures with an aqueous solution containing collagen having an average molecular weight of 300,000, a solid gel was precipitated. When using an aqueous solution containing collagen peptide having an average molecular weight of 7,000, suspension was slightly observed.

Example 1

An aqueous solution containing 5 wt % of a pine bark extract as used in Reference Example and an aqueous solution containing 5 wt % of epicatechin gallate were respectively prepared as a first liquid. Separately, an aqueous solution containing 1 wt % of collagen peptide having an average molecular weight of 1,000 was prepared as a second liquid. The first liquid and the second liquid were mixed as indicated in Table 2 below.

Next, three types of aqueous solutions were prepared respectively containing collagen peptide having an average molecular weight of 7,000, collagen peptide having an average molecular weight of 10,000, and collagen having an average molecular weight of 300,000 at 1 wt %, as a third liquid. The third liquid was added to the liquid mixture of the first liquid and the second liquid as indicated in Table 3 and mixed them. The resultant liquid mixture was allowed to stand at room temperature for one week, and it was visually observed whether or not coagulation-precipitation was caused in the liquid mixture. The results are shown in Table 3.

Examples 2 to 4

Instead of a collagen peptide having an average molecular weight of 1,000, collagen peptides having average molecular weights of 3,000 and 5,000 were used respectively to prepare a second liquid. Except that these were used, the liquid mixture containing a first liquid and a second liquid as indicated in Table 2 were prepared as in Example 1. The liquid mixture was treated as in Example 1, and it was visually observed whether or not coagulation-precipitation was caused in the finally obtained liquid mixture. The results are shown in Table 3.

Comparative Examples 1 to 4

Instead of a collagen peptide having an average molecular weight of 1,000, collagen peptide having an average molecular weight of 7,000, glycine, and water were used respectively to prepare a second liquid. Except that these were used, the liquid mixture containing a first liquid and a second liquid as indicated in Table 2 were prepared as in Example 1. The liquid mixture was treated as in Example 1, and it was visually observed whether or not coagulation-precipitation was caused in the finally obtained liquid mixture. The results are shown in Table 3.

TABLE 2

|  |  |  | Example | | | | Comparative Example | | | |
|---|---|---|---|---|---|---|---|---|---|---|
|  |  |  | 1 | 2 | 3 | 4 | 1 | 2 | 3 | 4 |
| First liquid | Pine bark extract | | 1 | 1 | 1 |  | 1 | 1 | 1 |  |
|  | Epicatechin gallate | | 1 | 1 | 1 | 1 | 1 | 1 | 1 | 1 |
| Second liquid | Collagen peptide: Average molecular weight | 1,000 | 20 |  |  |  |  |  |  |  |
|  |  | 3,000 |  | 20 |  | 20 |  |  |  |  |
|  |  | 5,000 |  |  | 20 |  |  |  |  |  |
|  |  | 7,000 |  |  |  |  | 20 |  |  |  |
|  | Glycine | |  |  |  |  |  | 20 |  |  |
|  | Water | |  |  |  |  |  |  | 20 | 20 |

Indicated by mL.

TABLE 3

|  |  |  | Type and content of third liquid | | | | | | | | |
|---|---|---|---|---|---|---|---|---|---|---|---|
|  |  |  | Collagen peptide: Average molecular weight 7,000 | | | Collagen peptide: Average molecular weight 10,000 | | | Collagen: Average molecular weight 300,000 | | |
|  |  |  | 2 mL | 20 mL | 60 mL | 2 mL | 20 mL | 60 mL | 2 mL | 20 mL | 60 mL |
| Ex. 1 | First liquid | Pine bark Catechin*¹ | − | − | − | − | − | − | − | − | − |
|  | Second liquid | 1,000*² | | | | | | | | | |
| Ex. 2 | First liquid | Pine bark Catechin*¹ | − | − | − | − | − | − | − | − | − |
|  | Second liquid | 3,000*² | | | | | | | | | |
| Ex. 3 | First liquid | Pine bark Catechin*¹ | − | − | − | − | − | − | − | − | − |
|  | Second liquid | 5,000*² | | | | | | | | | |
| Ex. 4 | First liquid | Catechin*¹ | − | − | − | − | − | − | − | − | − |
|  | Second liquid | 3,000*² | | | | | | | | | |
| Com. Ex. 1 | First liquid | Pine bark Catechin*¹ | − | − | − | − | ± | + | + | + | ± |
|  | Second liquid | 7,000*² | | | | | | | | | |
| Com. Ex. 2 | First liquid | Pine bark Catechin*¹ | − | − | − | + | + | + | + | + | + |
|  | Second liquid | Glycine | | | | | | | | | |
| Com. Ex. 3 | First liquid | Pine bark Catechin*¹ | − | − | − | + | + | + | + | + | + |
|  | Second liquid | Water | | | | | | | | | |
| Com. Ex. 4 | First liquid | Catechin*¹ | − | − | − | ± | ± | + | + | + | + |
|  | Second liquid | Water | | | | | | | | | |

+: The precipitation was remarkably observed, ±: The precipitation was slightly observed, −: The precipitation was not observed.
*¹Pine bark—Pine bark extract, Catechin—Epicatechin gallate
*²1,000, 3,000, 5,000, and 7,000—Average molecular weight of collagen peptide The results in Table 3 show that coagulation-precipitation is not caused when an aqueous solution containing collagen peptide or collagen having an average molecular weight of not less than 7,000 is mixed with the liquid mixture containing a flavan compound and a collagen peptide having an average molecular weight of less than 7,000 as shown in Examples 1 to 4. On the other hand, it is clear that coagulation-precipitation is caused when an aqueous solution containing collagen peptide or collagen having an average molecular weight of not less than 7,000 is mixed with the solution containing a flavan compound alone (Comparative Examples 3 and 4), or with the mixed liquid containing a flavan compound with collagen peptide having an average molecular weight of not less than 7,000 or an amino acid, glycine.

Example 5

An aqueous solution containing 5 wt % of a pine bark extract was prepared as a first liquid. Separately, an aqueous solution containing 1 wt % of collagen peptide having an average molecular weight of 1,000 was prepared as a second liquid. Furthermore, an aqueous solution containing 1 wt % of collagen peptide having an average molecular weight of 10,000 was prepared as a third liquid. The first liquid, the second liquid, and the third liquid were mixed as indicated in Table 4, using the following methods (Methods 1 to 3). The liquid mixture was evaluated for coagulation-precipitation or gelatinization immediately after mixing, and after allowed to stand for one day after mixing. The results are shown in Table 4.

(Method 1) after the first liquid and the second liquid are mixed, the third liquid is mixed with the obtained mixture.

(Method 2) after the second liquid and the third liquid are mixed, the first liquid is mixed with the obtained mixture.

(Method 3) after the first liquid and the third liquid are mixed, the second liquid is mixed with the obtained mixture.

Examples 6 to 16

As a first liquid, a second liquid, and a third liquid, aqueous solutions were prepared using materials listed in Table 4, in accordance with Example 5. The first liquid, the second liquid, and the third liquid were mixed as indicated in Table 4, using the three methods (Methods 1 to 3) as in Example 5. The liquid mixture was evaluated for coagulation-precipitation or gelatinization immediately after mixing, and after allowed to stand for one day after mixing. The results are shown in Table 4.

Comparative Examples 5 to 12

As a first liquid, a second liquid, and a third liquid, aqueous solutions were prepared using materials listed in Table 4, in accordance with Example 5. The first liquid, the second liquid, and the third liquid were mixed as indicated in Table 4, using the three methods (Methods 1 to 3) as in Example 5. The liquid mixture was evaluated for coagulation-precipitation or gelatinization immediately after mixing, and after allowed to stand for one day after mixing. The results are shown in Table 4.

TABLE 4

| | | | Example | | | | | | | | | | | | | Comparative Example | | | | | | | |
|---|---|---|---|---|---|---|---|---|---|---|---|---|---|---|---|---|---|---|---|---|---|---|---|
| | | | 5 | 6 | 7 | 8 | 9 | 10 | 11 | 12 | 13 | 14 | 15 | 16 | 5 | 6 | 7 | 8 | 9 | 10 | 11 | 12 |
| First liquid | Pine bark extract | | 1 | 1 | | | 1 | 1 | | | 1 | 1 | | | 1 | 1 | | | 1 | 1 | | |
| | Epicatechin gallate | | | | 1 | 1 | | | 1 | 1 | | | 1 | 1 | | | 1 | 1 | | | 1 | 1 |
| Second liquid | Collagen peptide: Average molecular weight | 1,000 | 20 | 20 | 20 | 20 | | | | | | | | | | | | | | | | |
| | | 3,000 | | | | | 20 | 20 | 20 | 20 | | | | | | | | | | | | |
| | | 5,000 | | | | | | | | | 20 | 20 | 20 | 20 | | | | | | | | |
| | Glycine | | | | | | | | | | | | | | 20 | 20 | 20 | 20 | | | | |
| | Water | | | | | | | | | | | | | | | | | | 20 | 20 | 20 | 20 |
| Third liquid | Collagen peptide or collagen: Average molecular weight | 10,000 | 20 | | 20 | | 20 | | 20 | | 20 | | 20 | | 20 | | 20 | | 20 | | 20 | |
| | | 300,000 | | 20 | | 20 | | 20 | | 20 | | 20 | | 20 | | 20 | | 20 | | 20 | | 20 |
| Method 1 | Immediately after mixing | | − | − | − | − | − | − | − | − | − | − | − | − | + | + | + | + | + | + | + | + |
| | Agitating the mixture for ten minutes | | − | − | − | − | − | − | − | − | − | − | − | − | + | + | + | + | + | + | + | + |
| Method 2 | Immediately after mixing | | + | + | + | + | + | + | + | + | + | + | + | + | + | + | + | + | + | + | + | + |
| | Agitating the mixture for ten minutes | | − | − | − | − | − | − | − | − | − | − | − | − | + | + | + | + | + | + | + | + |
| Method 3 | Immediately after mixing | | + | + | + | + | + | + | + | + | + | + | + | + | + | + | + | + | + | + | + | + |
| | Agitating the mixture for ten minutes | | − | − | − | − | − | − | − | − | − | − | − | − | + | + | + | + | + | + | + | + |

+: The precipitation was remarkably observed, ±: The precipitation was slightly observed, −: Not observed.

The results in Table 4 show that according to Example 5 to 16 a first liquid containing either one of a pine bark extract and epicatechin gallate, a second liquid containing a collagen peptide having an average molecular weight of less than 7,000, and a third liquid containing a collagen peptide or collagen having an average molecular weight of not less than 7,000 can be mixed in any order, and after mixing agitated the mixture for ten minutes to give a solutions without coagulation-precipitation. In particular, in the case of Method 1, coagulation-precipitation was not caused even immediately after mixing, and was not caused thereafter. Also in the cases of Methods 2 and 3, a clear aqueous solution was finally obtained without precipitation. On the other hand, in Comparative Examples in which a collagen peptide having an average molecular weight of less than 7,000 was not contained, coagulation-precipitation was formed in any mixing methods, and once the coagulation-precipitation was formed, the coagulation-precipitation was not disappeared even after agitation for ten minutes.

Example 17

A mixed powder was prepared by mixing a pine bark extract, a collagen peptide having an average molecular weight of 5,000, and a collagen peptide having an average molecular weight of 10,000 as indicated in Table 5. After 10 g of the mixed powder was dissolved in 100 mL of water, it was visually evaluated whether or not coagulation-precipitation or suspension was caused. The results are shown in Table 5.

Comparative Examples 13 and 14

Two types of mixed powders were prepared by mixing a pine bark extract, a collagen peptide having an average molecular weight of 5,000, and a collagen peptide having an average molecular weight of 10,000 as indicated in Table 5. After 10 g of the mixed powder was dissolved in 100 mL of water, it was visually evaluated whether or not coagulation-precipitation or suspension was caused. The results are shown in Table 5.

TABLE 5

|  |  | Ex. | Com. Ex. | |
| --- | --- | --- | --- | --- |
|  |  | 17 | 13 | 14 |
| Powder component | Pine bark extract (part by weight) | 2 | 2 | 2 |
|  | Collagen peptide 5,000*¹ (part by weight) | 99 | 0 | 198 |
|  | 10,000*¹ | 99 | 198 | 0 |
| Item | Coagulation-precipitation | – | – | – |
|  | Suspension | – | + | – |

+: The precipitation was remarkably observed. ±: The precipitation was slightly observed. –: Not observed.
*¹Average molecular weight The results in Table 5 show that according to Example 17 the mixed powder containing a flavan compound, a collagen peptide having an average molecular weight of less than 7,000, and a collagen peptide having an average molecular weight of not less than 7,000 can be dissolved in water without causing coagulation-precipitation or suspension. Using this mixed powder, coagulation-precipitation is not caused even in a case where wet granulation is performed with a liquid such as water or ethanol. Thus, granules uniformly containing the components can be obtained.

Example 18

Solution A was prepared by dissolving 5 parts by weight of a collagen peptide having an average molecular weight of 5,000 (produced by Nippi, incorporated) and 0.1 parts by weight of a pine bark extract in 40 parts by weight of water. Solution A was mixed with Solution B containing materials listed below at the ratio indicated below, and a collagen peptide-containing beverage was obtained. In this beverage, coagulation-precipitation is not caused by a flavan compound, or a flavan compound and a collagen peptide. Thus, there is no loss of the components, so that an excellent effect of improving blood flow and the like can be expected.
Solution B:

| Chondroitin-conjugated protein (MARUHA CORPORATION) | 0.1 parts by weight |
| --- | --- |
| Collagen peptide (Nippi, incorporated) (average molecular weight: 10,000) | 4 parts by weight |
| Tea leaf extract (Mitsui Norin Co., Ltd.) | 0.1 parts by weight |
| Glucose | 7 parts by weight |
| Orange peel (T. HASEGAWA CO., LTD.) | 0.1 parts by weight |
| Ascorbic acid | 0.1 parts by weight |
| Water | 43.5 parts by weight |

Example 19

Solution A was prepared by dissolving 0.6 parts by weight of silk peptide having an average molecular weight of 4,000 (produced by Ichimaru Pharcos Co., Ltd.) and 0.01 parts by weight of a pine bark extract in 30 parts by weight of water. Solution A was mixed with Solution B containing materials listed below at the ratio indicated below, and a skin lotion was obtained. Even with such a protein (peptide), coagulation-precipitation was not caused, and the skin lotion exhibited excellent moisturizing properties, effect of improving blood flow, and skin conditioning effect. It was found that in a case where peptide other than collagen is used, coagulation-precipitation caused by a flavan compound and coagulation-precipitation caused by a flavan compound and a high molecular weight peptide or protein can be suppressed as well.
Solution B:

| Collagen peptide (average molecular weight: 300,000) | 0.5 parts by weight |
| --- | --- |
| Elastin protein | 0.1 parts by weight |
| 0.05M sodium citrate | 20 parts by weight |
| 0.05M citric acid | 24.5 parts by weight |
| Butylene glycol | 1.0 parts by weight |
| Glycerin | 1.1 part by weight |
| Betaine | 0.1 parts by weight |
| Water | 22.09 parts by weight |

INDUSTRIAL APPLICABILITY

According to the present invention, a composition can be provided, wherein the composition includes a flavan compound, a protein degradation peptide having an average molecular weight of less than 7000, and a peptide or protein having an average molecular weight of not less than 7,000. In a case where the composition is formulated in a liquid preparation, the liquid preparation can be stable for a long period of time without coagulation-precipitation. Even if the precipitation is formed by either a flavan compound, or a flavan compound and a high molecular weight peptide or protein, the precipitation can be dissolved again by adding a protein degradation peptide having an average molecular weight of less than 7,000 to obtain a clear and stable solution. Accordingly, it is possible to avoid a loss of any components caused by precipitation in production. The composition of the present invention can be widely used as foods, drugs, quasi-drugs, cosmetics, and the like in various forms.

The invention claimed is:
1. A flavan compound-containing composition, comprising:
 a proanthocyanidin;
 a protein degradation peptide having an average molecular weight of less than 7,000; and
 a peptide or protein having an average molecular weight of not less than 7,000,
 wherein the proanthocyanidin comprises at least 1 part by weight of proanthocyanidin having a degree of polymerization of 2 to 4 with respect to 1 part by weight of proanthocyanidin having a degree of polymerization of 5 or more.
2. A flavan compound-containing liquid composition, comprising:
 a proanthocyanidin;
 a protein degradation peptide having an average molecular weight of less than 7,000;
 a peptide or protein having an average molecular weight of not less than 7,000; and
 a solvent,
 wherein,
 the proanthocyanidin comprises at least 1 part by weight of proanthocyanidin having a degree of polymer- ization of 2 to 4 with respect to 1 part by weight of proanthocyanidin having a degree of polymerization of 5 or more.

3. A method for producing the liquid composition of claim 2, comprising the steps of:
   mixing, in a solvent, a flavan compound that is at least one of proanthocyanidin and catechins with a protein degradation peptide having an average molecular weight of less than 7,000; and
   adding a peptide or protein having an average molecular weight of not less than 7,000 to the obtained mixture and mixing them.

4. A method for producing the liquid composition of claim 2, comprising the step of:
   dissolving coagulation-precipitation caused in a solution containing a flavan compound that is at least one of a proanthocyanidin and catechins and a peptide or protein having an average molecular weight of not less than 7,000, by adding and mixing a protein degradation peptide having an average molecular weight of less than 7,000 in the solution.

* * * * *